(12) United States Patent
Terrisse et al.

(10) Patent No.: US 9,579,271 B2
(45) Date of Patent: Feb. 28, 2017

(54) ANHYDROUS FOAMING COMPOSITION

(75) Inventors: Isabelle Terrisse, Vitry sur Seine (FR); Celine Philippon, L'hay les Roses (FR)

(73) Assignee: L'OREAL, Paris (FR)

( * ) Notice: Subject to any disclaimer, the term of this patent is extended or adjusted under 35 U.S.C. 154(b) by 213 days.

(21) Appl. No.: 13/978,449

(22) PCT Filed: Jan. 2, 2012

(86) PCT No.: PCT/EP2012/050011
§ 371 (c)(1),
(2), (4) Date: Sep. 17, 2013

(87) PCT Pub. No.: WO2012/093102
PCT Pub. Date: Jul. 12, 2012

(65) Prior Publication Data
US 2014/0031305 A1     Jan. 30, 2014

Related U.S. Application Data

(60) Provisional application No. 61/436,273, filed on Jan. 26, 2011.

(30) Foreign Application Priority Data

Jan. 4, 2011   (FR) ..................................... 11 50041

(51) Int. Cl.
| | | |
|---|---|---|
| *A61K 8/42* | (2006.01) | |
| *A61K 8/60* | (2006.01) | |
| *A61K 8/44* | (2006.01) | |
| *A61K 8/73* | (2006.01) | |
| *A61K 8/02* | (2006.01) | |
| *A61K 8/04* | (2006.01) | |
| *A61Q 1/14* | (2006.01) | |
| *A61K 8/97* | (2006.01) | |
| *A61Q 19/00* | (2006.01) | |

(52) U.S. Cl.
CPC .............. *A61K 8/602* (2013.01); *A61K 8/027* (2013.01); *A61K 8/0241* (2013.01); *A61K 8/046* (2013.01); *A61K 8/42* (2013.01); *A61K 8/44* (2013.01); *A61K 8/60* (2013.01); *A61K 8/731* (2013.01); *A61K 8/97* (2013.01); *A61Q 1/14* (2013.01); *A61Q 19/00* (2013.01); *A61K 2800/31* (2013.01)

(58) Field of Classification Search
None
See application file for complete search history.

(56) References Cited

U.S. PATENT DOCUMENTS

| | | | | |
|---|---|---|---|---|
| 5,728,389 | A * | 3/1998 | Sebillotte-Arnaud | ........ 424/400 |
| 5,951,991 | A * | 9/1999 | Wagner et al. | ................ 424/401 |
| 6,306,408 | B1 * | 10/2001 | Eichhorn | ............. A61K 8/0208 |
| | | | | 424/401 |
| 6,338,855 | B1 * | 1/2002 | Albacarys | ............ A61K 8/0208 |
| | | | | 424/402 |
| 6,649,584 | B2 * | 11/2003 | Wisniewski | ......... A61K 8/0208 |
| | | | | 134/42 |
| 2003/0024556 | A1 | 2/2003 | Guiramand et al. | |

FOREIGN PATENT DOCUMENTS

| | | | | |
|---|---|---|---|---|
| CN | 1781479 | * | 6/2006 | .............. A61P 35/00 |
| EP | 0 692 240 | | 1/1996 | |
| FR | 2 779 648 | | 12/1999 | |
| FR | 2 824 265 | | 11/2002 | |
| FR | 2 921 264 | | 3/2009 | |

OTHER PUBLICATIONS

English language machine translation of CN1791479 above, downloaded May 1, 2015 from EPO.*
Dave, Rutesh H., "Overview of pharmaceutical excipients used in tablets and capsules" Drug Topics (2008) pp. 1-12, downloaded from drugtopics.modernmedicine.com.*
International Search Report Issued Apr. 12, 2012 in PCT/EP12/50011 Filed Jan. 2, 2012.

\* cited by examiner

*Primary Examiner* — Eric Olson
(74) *Attorney, Agent, or Firm* — Oblon, McClelland, Maier & Neustadt, L.L.P.

(57) ABSTRACT

The subject-matter of the present invention is an anhydrous cosmetic composition comprising, in a physiologically acceptable medium: —at least one nonionic surfactant, at least one anionic surfactant, at least 25% of at least one filler. The article is partially or completely soluble in water and it constitutes a foaming product used for cleansing the skin and hair and/or removing makeup from the skin and/or as scrubbing product.

22 Claims, No Drawings

ANHYDROUS FOAMING COMPOSITION

CROSS REFERENCE TO RELATED APPLICATIONS

The present application is a 35 U.S.C. §371 national stage patent application of International patent application PCT/EP2012/050011, filed on Jan. 2, 2012, published as WO/2012/093102 on Jul. 12, 2012, the text of which is incorporated by reference, and claims the benefit of the filing date of French application no. 1150041, filed on Jan. 4, 2011, and U.S. Provisional application 61/436,273, filed on Jan. 26, 2011, the text of both of which is also incorporated by reference.

The present invention relates to an anhydrous foaming composition comprising anionic and nonionic surfactants and at least 25% of fillers and/or fibres, and to the use thereof for cleansing and/or removing makeup from keratinous substances.

Foaming compositions in the liquid form require the use of a gelling or thickening agent, such as, for example, gums, in order to exhibit a satisfactory consistency. However, these gums may exhibit the disadvantage of inhibiting the development of the foam.

For these reasons, it may be advantageous to provide foaming products in the solid form which do not comprise water or which comprise very little water and which, in addition, exhibit the advantage of preventing microbiological problems and thus of not requiring the use of preservatives.

For example, the document FR 2 779 684 teaches solid compositions in the form of a deformable paste based on specific pulverulent fillers and anionic surfactants. These compositions can only be obtained using an extruder, which can be restrictive in processing terms.

Furthermore, for some years, the cosmetic market has been marked by a very high demand for formulations comprising ingredients of natural origin. Consumers desire formulations devoid of chemicals, to which they prefer ingredients of natural origin which are renowned for their better tolerance and affinity with the skin and which are more environmentally friendly.

A search is thus underway to obtain foaming cleansing products comprising compounds of natural origin which are satisfactorily harmless with regard to keratinous substances, which exhibit good microbiological preservation, and which are easily and pleasant to use while nevertheless having the properties required for foaming products, namely good mixing with water, rapid transformation into foam and good rinsing.

"Natural compound" is understood to mean a compound which is obtained directly from the earth or soil or from plants or animals via, if appropriate, one or more physical processes such as, for example, a grinding, a refining, a distillation, a purification or a filtration.

Compounds "of natural origin" is understood to mean a natural compound which has been subjected to one or more additional chemical or industrial treatments, bringing about modifications which do not affect the essential qualities of this compound, and/or a compound predominantly comprising natural constituents which have or have not been subjected to transformations, as indicated above.

Mention may be made, as nonlimiting example of additional chemical or industrial treatment bringing about modifications which do not affect the essential qualities of a natural compound, of those allowed by the controlling bodies, such as Ecocert (Reference system for biological and ecological cosmetic products, January 2003), or defined in recognized handbooks in the field, such as Cosmetics and Toiletries Magazine, 2005, Vol. 120, 9:10.

The Applicant Company has discovered that an anhydrous composition comprising a specific combination of anionic and nonionic surfactants and a high content of fillers makes it possible to achieve these objectives.

More specifically, a subject-matter of the invention is an anhydrous cosmetic composition comprising, in a physiologically acceptable medium:
- at least one nonionic surfactant,
- at least one anionic surfactant,
- at least 25% of particles chosen from fillers, fibres and their mixtures.

The compositions according to the invention, after contributing water, exhibit good initiation of foam and a smooth and copious form.

"Anhydrous" composition is understood to mean a composition comprising less than 0.5% of water, preferably entirely devoid of water.

Another subject-matter of the invention is a method for cleansing or removing makeup from keratinous substances, such as the skin, including the scalp, keratinous fibres, such as the eyelashes or hair, and/or lips, characterized in that a cosmetic composition as defined above is applied to the said keratinous substances.

The composition according to the invention is intended for topical application and thus comprises a physiologically acceptable medium. "Physiologically acceptable medium" is understood here to mean a medium compatible with keratinous substances, such as the skin, mucous membranes, scalp, eyes and/or keratinous fibres, such as the eyelashes or hair.

Nonionic Surfactants

The nonionic surfactants can be chosen, for example, from phospholipids, alkyl polyglucosides (APG), maltose esters, sucrose esters, hydrophobicized gums, polyglycerolated fatty alcohols, esters of glycerol and of a fatty acid, oxyalkylenated glycerol esters, oxyalkylenated sugar esters, polyethylene glycol fatty acid esters, esters of a fatty acid and of sorbitan, glucamine derivatives, such as 2-ethylhexyloxycarbonyl-N-methylglucamine, and their mixtures. The phospholipids used in the composition according to the invention can be of vegetable or animal origin and can be provided in the pure form or in the form of a mixture.

The phospholipids used in the composition can in particular be lecithins, which are a complex mixture of phosphatides mainly chosen from phosphatidic acid, phosphatidylcholine, phosphatidylethanolamine, phosphatidylserine, lysophosphatidylcholine and/or phosphatidylinositol, in combination with variable amounts of other substances, such as triglycerides, glycolipids, sphingolipids, fatty acids and carbohydrates.

It will thus be possible to choose either the phospholipids mentioned above or the lecithins comprising these phospholipids.

According to a specific embodiment of the invention, the phospholipid or phospholipids are chosen from nonhydrogenated lecithins and hydrogenated lecithins.

Nonhydrogenated lecithins are generally obtained by lipid extraction, using nonpolar solvents, from vegetable or animal fatty substances. This lipid fraction usually comprises, predominantly, glycerophospholipids, including phosphatidylcholine.

The animal or vegetable sources which can be used to extract the nonhydrogenated lecithins are, for example, soya, sunflower or eggs. The glycerophospholipids included, in high proportion, in these lecithins are mainly phosphatidylcholine and phosphatidylethanolamine.

The nonhydrogenated lecithins suitable for the implementation of the present invention can be lecithins resulting from soya, sunflower, eggs and/or their mixtures.

The lecithins are normally supplied in the form dissolved in fatty acids, triglycerides or other solvents or in the form of powders or cakes.

These are usually mixtures of lecithins, the glycerophospholipid content of which, in the products as sold, generally vary from approximately at least 15% to approximately at least 95%.

Mention may be made, among the nonhydrogenated lecithins which may be suitable for the implementation of the cosmetic compositions in accordance with the present invention, of lecithins sold under the references Nattermann Phospholipid®, Phospholipon 80® and Phosale 75® by American Lecithin Company, Epikuron 145V, Topcithin 300, Emulmetik 930, Ovothin 200 and Organic Lecithin, which are sold by Lucas Meyer.

The hydrogenated lecithins are obtained by controlled hydrogenation of the nonhydrogenated lecithins as described above.

Mention may be made, as hydrogenated lecithins which can be used in the composition according to the invention, for example, of that which is sold under the reference Nikkol Lecinol S 10 by Nikko.

Use is preferably made, as alkyl polyglucosides, of those comprising an alkyl group comprising from 6 to 30 carbon atoms and preferably from 8 to 16 carbon atoms and comprising a hydrophilic (glucoside) group preferably comprising from 1.2 to 3 saccharide units. Mention may be made, for example, of decyl glucoside ($C_9/C_{11}$ alkyl polyglucoside (1.4)), such as the product sold under the name Mydol 10® by Kao Chemicals, the product sold under the name Plantaren 2000 UP® by Cognis and the product sold under the name Oramix NS 10® by Seppic; caprylyl/capryl glucoside, such as the product sold under the name Oramix CG 110® by Seppic or Plantacare 810 P by Cognis; lauryl glucoside, such as the products sold under the names Plantaren 1200 N® and Plantacare 1200® by Cognis; coco glucoside, such as the product sold under the name Plantacare 818/UP® by Cognis; cetearyl glucoside, optionally as a mixture with cetearyl alcohol, sold, for example, under the name Montanov 68 by Seppic, under the name Tego-Care CG90 by Goldschmidt and under the name Emulgade KE3302 by Henkel; arachidyl glucoside, for example in the form of the mixture of arachidyl and behenyl alcohols and of arachidyl glucoside sold under the name Montanov 202 by Seppic; cocoyl ethyl glucoside, for example in the form of the mixture (35/65) with cetyl and stearyl alcohols, sold under the name Montanov 82 by Seppic; or $C_{12}$ to $C_{20}$ alkyl glucosides, such as those sold as a mixture with $C_{14}$ to $C_{22}$ fatty alcohols under the reference Montanov L by Seppic.

The oxyalkylenated glycerol esters are in particular the polyoxyethylenated derivatives of esters of glycerol and of a fatty acid and of their hydrogenated derivatives. These oxyalkylenated glycerol esters can be chosen, for example, from esters of glycerol and of fatty acids which are hydrogenated and oxyethylenated, such as PEG-200 hydrogenated glyceryl palmate, sold under the name Rewoderm LI-S 80 by Goldschmidt; oxyethylenated glycerol cocoates, such as PEG-7 glyceryl cocoate, sold under the name Tegosoft GC by Goldschmidt, and PEG-30 glyceryl cocoate, sold under the name Rewoderm LI-63 by Goldschmidt; and their mixtures.

The oxyalkylenated sugar esters are in particular polyethylene glycol ethers of fatty acid and sugar esters. These oxyalkylenated sugar esters can be chosen, for example, from oxyethylenated glucose esters, such as PEG-120 methyl glucose dioleate, sold under the name Glucamate DOE 120 by Amerchol.

The polyethylene glycol fatty acid esters are preferably $C_{16}$-$C_{22}$ fatty acid esters comprising from 8 to 100 ethylene oxide units.

The fatty chain of the esters can be chosen in particular from the stearyl, behenyl, arachidyl, palmityl or cetyl units and their mixtures, such as cetearyl, and preferably a stearyl chain.

The number of ethylene oxide units can range from 8 to 100, preferably from 10 to 80 and better still from 10 to 50. According to a specific embodiment of the invention, this number can range from 20 to 40.

Mention may be made, as example of polyethylene glycol fatty acid ester, of stearic acid esters respectively comprising 20, 30, 40, 50 and 100 ethylene oxide units, such as the products respectively sold under the names Myrj 49 P (polyethylene glycol 20 EO stearate; CTFA name: PEG-20 stearate), Myrj 51, Myrj 52 P (polyethylene glycol 40 EO stearate; CTFA name: PEG-40 stearate), Myrj 53 and Myrj 59 P by Croda.

The esters of a $C_{16}$-$C_{22}$ fatty acid and of sorbitan are in particular esters of $C_{16}$-$C_{22}$ acids and of sorbitan and are formed by esterification with sorbitol of at least one fatty acid comprising at least one saturated or unsaturated linear alkyl chain respectively having from 16 to 22 carbon atoms. These esters can be chosen in particular from sorbitan stearates, behenates, arachidonates, palmitates or oleates, and their mixtures. Use is preferably made of sorbitan stearates and palmitates, and preferably sorbitan stearates. Mention may be made, as example of sorbitan ester which can be used in the composition according to the invention, of sorbitan monostearate (CTFA name: Sorbitan stearate), sold by Croda under the name Span 60, sorbitan tristearate, sold by Croda under the name Span 65 V, sorbitan monopalmitate (CTFA name: Sorbitan palmitate), sold by Croda under the name Span 40, sorbitan monooleate, sold by Croda under the name Span 80 V, or sorbitan trioleate, sold by Uniqema under the name Span 85 V. Preferably, the sorbitan ester used is sorbitan tristearate.

The esters of glycerol and of a fatty acid can be obtained in particular from an acid comprising a saturated linear alkyl chain having from 16 to 22 carbon atoms. Mention may in particular be made, as ester of glycerol and of a fatty acid, of glyceryl stearate (glyceryl mono-, di- and/or tristearate) (CTFA name: Glyceryl stearate), glyceryl ricinoleate, and their mixtures. Preferably, the ester of glycerol and of a fatty acid used is chosen from glyceryl stearates.

Mention may also be made of the mixture of glyceryl stearate and of polyethylene glycol 100 EO monostearate and in particular that comprising a 50/50 mixture sold under the name Arlacel 165 by Croda.

The esters of sucrose and of fatty acids are preferably chosen from the esters resulting from the reaction of sucrose(s) (saccharose) and fatty acid(s) comprising from 10 to 24 carbon atoms, preferably from 12 to 20 carbon atoms, better still from 12 to 18 carbon atoms and even better still from 12 to 16 carbon atoms.

The fatty acids comprising from 10 to 24 carbon atoms can be saturated or unsaturated and linear or branched.

The fatty acids can be chosen from oleic acid, lauric acid, palmitic acid, myristic acid, stearic acid, linoleic acid, capric acid or their mixtures.

According to one embodiment, the ester of sucrose and of a fatty acid is chosen from the esters resulting from the reaction of sucrose and of a fatty acid comprising from 12 to 18 carbon atoms, preferably from 12 to 16 carbon atoms, such as lauric acid and/or palmitic acid, such as, for example, sucrose laurate, sucrose palmitate or a mixture.

The esters of sucrose and of fatty acids can be chosen from mono-, di-, tri- and tetraesters, polyesters and their mixtures. Use is preferably made of esters having a low degree of esterification such as, for example, monoesters, diesters or triesters of sucrose and of a fatty acid or a mixture. The ester of sucrose and of a fatty acid can be provided in the form of a mixture of esters having a low degree of esterification, such as, for example, a mixture of monoester and diester or a mixture of monoester, diester and triester.

In the case where use is made of a mixture of esters of sucrose and of a fatty acid, preference is given to a mixture in which the esters having a low degree of esterification, in particular the monoesters, are predominant and represent, for example, at least 50% by weight, preferably at least 60% by weight, of the mixture of esters of sucrose and of a fatty acid.

Use may in particular be made of a mixture of esters of sucrose and of fatty acids comprising from 12 to 16 carbon atoms, in particular a mixture of mono-, di- and triesters of lauric acid or palmitic acid, it being possible for the said mixture to comprise a minor amount (in a content of less than or equal to 40% by weight, with respect to the weight of the mixture of esters of sucrose and of a fatty acid) of esters of sucrose and of fatty acids in which the fatty acid comprises more than 16 carbon atoms.

Preferably, the ester of sucrose and of a fatty acid used in the present invention exhibits an HLB of greater than or equal to 10, preferably of greater than or equal to 12.

As is well known, HLB (Hydrophilic-Lipophilic Balance) is understood to mean the equilibrium between the size and the strength of the hydrophilic group and the size and the strength of the lipophilic group of the surface-active agent.

The HLB value according to Griffin is defined in J. Soc. Cosm. Chem., 1954 (volume 5), pages 249-256.

Mention may be made, as examples of esters or of mixtures of esters of sucrose and of a fatty acid of:

Surfhope SE Cosme C-1416, exhibiting an HLB of 16, which is a sucrose myristate comprising approximately 80% of monoester, the remainder of the mixture being composed of di- and triesters, Surfhope SE Cosme C-1216, the INCI name of which is sucrose laurate, with an HLB equal to 16 and comprises from 75 to 90% of monoester, the remainder of the mixture being composed of di- and triesters, Surfhope SE Cosme C-1215L, the INCI name of which is sucrose laurate, with an HLB equal to 15, comprising approximately 70% of monoesters, the remainder of the mixture being composed of diesters and other polyesters, Surfhope SE Cosme C-1616, exhibiting an HLB of 16, which is a mixture of esters of sucrose and of palmitic and/or stearic acids (INCI name: Sucrose palmitate), comprising from 75 to 90% of monoester, the remainder of the mixture being composed of di- and triesters, and which can comprise sucrose stearate and sucrose palmitate/stearate.

Mention may also be made of the ester carrying the INCI name Sucrose laurate, sold by Dai-ichi Seiyaku under the reference DK ester S-L18A, with an HLB equal to 17, comprising 70% of monoesters and 30% of di- and triesters.

Mention may also be made, as examples of esters or mixtures of esters of sucrose and of a fatty acid, or:

the products sold under the names F160, F140, F110, F90, F70 and SL40 by Crodesta, respectively denoting sucrate palmitate/stearates formed of 73% of monoester and 27% of di- and triester, of 61% of monoester and 39% of di-, tri-, and tetraester, of 52% of monoester and 48% of di-, tri-, and tetraester, of 45% of monoester and 55% of di-, tri- and tetraester, of 39% of monoester and 61% of di-, tri- and tetraester, and sucrose monolaurate;

the products sold under the name Ryoto Sugar Esters, for example referenced B370 and corresponding to the sucrose behenate formed of 20% of monoester and 80% of di-, tri- and polyester;

the sucrose mono- and dipalmitate/stearate sold by Goldschmidt under the name Tegosoft PSE.

According to one embodiment, sucrose laurate is used.

According to one embodiment, the composition comprises at least one nonionic surfactant chosen from esters of sucrose, in particular sucrose laurate.

The amount of nonionic surfactants can range, for example, from 0.1 to 20% by weight, preferably from 0.5 to 15% by weight, better still from 1 to 10% by weight and even better still from 2 to 8% by weight, with respect to the total weight of the composition.

Anionic Surfactants

The anionic surfactants can be chosen in particular from anionic derivatives of proteins of vegetable origin, amino acids and amino acid derivatives, alkyl sulphates, alkyl ether sulphates, sulphonates, isethionates, taurates, sulphosuccinates, alkyl sulphoacetates, phosphates and alkyl phosphates, polypeptides, anionic derivatives of alkyl polyglucoside, soaps (salts of fatty acids), soybean oil derivatives, lactic acid derivatives, their salts and their mixtures.

The anionic derivatives of proteins of vegetable origin are protein hydrolysates comprising a hydrophobic group, it being possible for the said hydrophobic group to be naturally present in the protein or to be added by reaction of the protein and/or protein hydrolysate with a hydrophobic compound. The proteins are of vegetable origin and the hydrophobic group can in particular be a fatty chain, for example an alkyl chain comprising from 10 to 22 carbon atoms.

Mention may more particularly be made, as anionic derivatives of proteins of vegetable origin which can be used in the composition according to the invention, of wheat, soya, oat or silk protein hydrolysates comprising an alkyl chain having from 10 to 22 carbon atoms, and their salts. The alkyl chain can in particular be a lauryl chain and the salt can be a sodium, potassium and/or ammonium salt. Mention may be made, for example, of the sodium, potassium and/or ammonium salts of protein hydrolysates where the protein is a silk protein modified by lauric acid, such as the product sold under the name Kawa Silk by Kawaken; the sodium, potassium and/or ammonium salts of protein hydrolysates where the protein is a wheat protein modified by lauric acid, such as the potassium salt sold under the name Aminofoam W OR by Croda (CTFA name: Potassium lauroyl wheat amino acids) and the sodium salt sold under the name Proteol LW 30 by Seppic (CTFA name: Sodium lauroyl wheat amino acids); the sodium, potassium and/or ammonium salts of protein hydrolysates with a protein as an oat protein comprising an alkyl chain having from 10 to 22 carbon atoms and more especially the sodium, potassium and/or ammonium salts of protein hydrolysates where the protein is an oat protein modified by lauric acid, such as the sodium salt sold under the name Proteol Oat (CTFA name:

Sodium lauroyl oat amino acids); Proteol SAV 50S (INCI name: Sodium cocoyl amino acid), Proteol APL (INCI name: Sodium cocoyl apple amino acids), sold by Seppic, Amaranth S (INCI name: Sodium cocoyl hydrolyzed amaranth proteins) and their mixtures.

Mention may be made, as alkyl ether sulphates, for example, of sodium lauryl ether sulphate (70/30 $C_{12}$-$C_{14}$) (2.2 EO), sold under the names Sipon AOS 225® or Texapon N702 Paté® by Cognis, ammonium lauryl ether sulphate (70/30 $C_{12}$-$C_{14}$) (3 EO), sold under the name Sipon LEA 370® by Cognis, or ammonium ($C_{12}$-$C_{14}$)alkyl ether (9 EO) sulphate, sold under the name Rhodapex AB/20® by Rhodia Chimie.

Mention may be made, as sulphonates, for example, of α-olefinsulphonates, such as sodium α-olefinsulphonate ($C_{14}$-$C_{16}$), sold under the name Bio-Terge AS-40® by Stepan, sold under the names Witconate AOS Protégé® and Sulframine AOS PH 12® by Witco or sold under the name Bio-Terge AS-40 CG® by Stepan, secondary sodium olefinsulphonate, sold under the name Hostapur SAS 30® by Clariant; or linear alkylarylsulphonates, such as sodium xylenesulphonate, sold under the names Manrosol SXS30®, Manrosol SX540® and Manrosol SX593® by Manro. Mention may also be made of the mixture Mention may be made, as alkyl sulphoacetates, of lauryl sulphoacetate, such as, for example, that which is sold as a mixture with sodium methyl-2 sulpholaurate and disodium 2-sulpholaurate under the reference Stepan Mild PCL by Stepan.

Mention may be made, as isethionates, of acylisethionates, such as sodium cocoylisethionate, for example the product sold under the name Jordapon CI P® by Jordan.

Mention may be made, as taurates, of the sodium salt of palm kernel oil methyltaurate, sold under the name Hostapon CT Paté® by Clariant; N-acyl-N-methyltaurates, such as sodium N-cocoyl-N-methyltaurate, sold under the name Hostapon LT-SF® by Clariant or sold under the name Nikkol CMT-30-T® by Nikkol, or sodium palmitoyl methyltaurate, sold under the name Nikkol PMT® by Nikkol.

Mention may be made, as sulphosuccinates, for example, of oxyethylenated (3 EO) lauryl (70/30 $C_{12}$/$C_{14}$) alcohol monosulphosuccinate, sold under the names Setacin 103 Special® and Rewopol SB-FA 30 K 4® by Witco, the disodium salt of a hemisulphosuccinate of $C_{12}$-$C_{14}$ alcohols, sold under the name Setacin F Special Paste® by Zschimmer Schwarz, oxyethylenated (2 EO) disodium oleamidosulphosuccinate, sold under the name Standapol SH 135® by Cognis, oxyethylenated (5 EO) lauramide monosulphosuccinate, sold under the name Lebon A-5000® by Sanyo, the disodium salt of oxyethylenated (10 EO) lauryl citrate monosulphosuccinate, sold under the name Rewopol SB CS 50® by Witco, the disodium salt of lauryl alcohol monosulphosuccinate, sold under the name Rewopol SB F12P® by Witco, or ricinoleic monoethanolamide monosulphosuccinate, sold under the name Rewoderm S 1333® by Witco.

Mention may be made, as phosphates and alkyl phosphates, for example, of monoalkyl phosphates and dialkyl phosphates, such as lauryl monophosphate, sold under the name MAP 20® by Kao Chemicals, the potassium salt of dodecyl phosphate, a mixture of mono- and diester (predominantly diester) sold under the name Crafol AP-31® by Cognis, the mixture of octyl phosphate monoester and diester, sold under the name Crafol AP-20® by Cognis, the mixture of ethoxylated (7 mol of EO) 2-butyloctyl phosphate monoester and diester, sold under the name Isofol 12 7 EO-Phosphate Ester® by Condea, the potassium or triethanolamine salt of mono($C_{12}$-$C_{13}$)alkyl phosphate, sold under the references Arlatone MAP 230K-40® and Arlatone MAP 230T-60® by Uniqema, or potassium lauryl phosphate, sold under the name Dermalcare MAP XC-99/09® by Rhodia Chimie.

The anionic alkyl polyglucoside derivatives can in particular be citrates, tartrates, sulphosuccinates, carbonates and glycerol ethers obtained from alkyl polyglucosides. Mention may be made, for example, of the sodium salt of cocoyl polyglucoside (1,4) tartaric ester, sold under the name Eucarol AGE-ET® by Cesalpinia, the disodium salt of cocoyl polyglucoside (1,4) sulphosuccinic ester, sold under the name Essai 512 MP® by Seppic, or the sodium salt of cocoyl polyglucoside (1,4) citric ester, sold under the name Eucarol AGE-EC® by Cesalpinia.

The soaps are obtained from a fatty acid which is partially or completely saponified (neutralized) with a basic agent. These are alkali metal or alkaline earth metal soaps or soaps of organic bases. Use may be made, as fatty acids, of saturated, linear or branched fatty acids comprising from 8 to 30 carbon atoms and preferably comprising from 8 to 22 carbon atoms. This fatty acid can be chosen in particular from palmitic acid, stearic acid, myristic acid, lauric acid and their mixtures.

Use may be made, as basic agents, for example, of alkali metal hydroxides (sodium hydroxide or potassium hydroxide), alkaline earth metal hydroxides (for example magnesium hydroxide), ammonium hydroxide or organic bases, such as triethanolamine, N-methylglucamine, lysine and arginine.

The soaps can in particular be fatty acid alkali metal salts, the basic agent being an alkali metal hydroxide and preferably potassium hydroxide (KOH).

The amount of basic agent must be sufficient for the fatty acid to be at least partially neutralized.

Mention may in particular be made of sodium or potassium laurate, potassium myristate, potassium palmitate, potassium stearate, potassium cocoate or salts of stearic acid and KOH formed in situ.

The soybean oil derivatives and their salts are in particular the fatty acids and salts of fatty acids derived from soybean oil (the INCI name of which is "glycine soya oil" or "soybean oil") and in particular the salts of alkali metals, such as Na, Li or K, preferably Na or K, and of fatty acids resulting from soya, such as potassium soyate, such as, for example, that which is sold by Noveon.

Mention may be made, as acylamino acids, for example, of sodium cocoyl glycinate, sold by Ajinomoto under the name Amilite GCS-12, alaninates and their derivatives, such as that which is sold under the name Amilite ACS-12 by Amilon, sodium cocoyl glycinate, sold by Ajinomoto under the name Amilite GCK-12, disodium cocoyl glutamate, sold by Ajinomoto under the name Amisoft ECS-22SB, sodium lauroyl glutamate, sold by Ajinomoto under the name Amisoft LS11, sodium lauroyl sarcosinate, sold by Seppic under the name Oramix L 30, sodium and disodium stearoyl glutamate, sold by Ajinomoto under the names Amisoft HS21 P and HS11 Pf, and sodium cocoyl sarcosinate, sold by Zschimmer & Schwarz under the name Protelan LS 9011/C. Mention may also be made of the sodium salt of lauroyl oat amino acids, such as Proteol Oat sold by Seppic, or the compound carrying the INCI name sodium cocoylamino acids, such as Proteol SAV 5OS from Seppic.

The amino acid derivatives can be chosen, for example, from sarcosinates and in particular acylsarcosinates, such as sodium lauroylsarcosinate, sold under the name Sarkosyl NL 97® by Ciba or sold under the name Oramix L 30® by Seppic, sodium myristoyl sarcosinate, sold under the name Nikkol Sarcosinate MN® by Nikkol, or sodium palmitoyl sarcosinate, sold under the name Nikkol Sarcosinate PN® by Nikkol; alaninates, such as sodium N-lauroyl-N-methyl-amidopropionate, sold under the name Sodium Nikkol Alaninate LN 30® by Nikkol or sold under the name Alanone Ale®, by Kawaken, and triethanolamine N-lauroyl-N-methylalanine, sold under the name Alanone Alta® by Kawaken; aspartates, such as the mixture of triethanolamine N-lauroyl aspartate and triethanolamine N-myristoyl aspartate, sold under the name Asparack® by Mitsubishi; or citrates.

Mention may also be made of the alkali metal salts of ($C_{10}$-$C_{22}$)acylglutamic acids, preferably an alkali metal salt of ($C_{12}$-$C_{20}$)acylglutamic acids, for example an alkali metal salt of ($C_{16}$-$C_{18}$)acylglutamic acids. The alkali metal salts are, for example, the sodium salts, potassium salts and lithium salts, preferably the sodium salts.

It can be in particular one of the alkali metal salts of stearoyl glutamic acid, lauroyl glutamic acid, $C_{16}$ acyl glutamic acid, myristoyl glutamic acid, cocoyl glutamic acid or hydrogenated tallow acyl glutamic acid.

Preferably, the ionic surfactant will be an ionic surfactant chosen from sodium stearoyl glutamate, disodium stearoyl glutamate, potassium stearoyl glutamate, sodium lauroyl glutamate, disodium lauroyl glutamate, potassium lauroyl glutamate, sodium cocoyl glutamate, sodium hydrogenated tallow acyl glutamate and their mixtures, preferably sodium stearoyl glutamate.

Mention may be made, by way of illustration, for example, of the sodium stearoyl glutamate sold by Ajinomoto under the reference Amisoft HS 11 PF®.

The lactic acid derivatives or their salts can be chosen from acyl lactylic acid derivatives or their salts (lactylates), such as stearoyl lactylate, such as, for example, that sold by Oleon NV under the name Radiamuls 2980; sodium stearoyl lactylate, such as provided, for example, by Oleon NV under the name Radiamuls 2990, by Karlshamns AB under the name Akoline SL, by Uniqema under the name Priazul 2134 or by Dr Straetmans under the name Dermofeel SL; sodium isostearoyl lactylate, such as that sold by Uniqema under the name Priazul 2133; sodium behenoyl lactylate, for example sold by Rita Corporation under the name Pationic SBL; sodium cocoyl lactylate, such as that sold by Rita under the name Pationic SCL; sodium oleoyl lactylate; sodium lauroyl lactylate (Pationic 138C from Caravan); or sodium caproyl lactylate (Capmul S8L-G from Abitec).

Mention may also be made of the sodium cocoamphoacetate, glycerin, lauryl glucoside, sodium cocoyl glutamate and sodium lauryl glucose carboxylate mixture sold by Cognis under the reference Plantapon SF.

According to one embodiment, use is made of at least one anionic surfactant chosen from the alkali metal salts of ($C_{10}$-$C_{22}$)acylglutamic acid, preferably an alkali metal salt of ($C_{12}$-$C_{20}$)acylglutamic acids, for example an alkali metal salt of ($C_{16}$-$C_{18}$)acylglutamic acids.

The anionic surfactants can be present in a content ranging from 0.1 to 20% by weight, preferably from 0.5 to 15% by weight, better still from 1 to 10% by weight and even better still from 2 to 8% by weight, with respect to the total weight of the composition.

Additional Foaming Agents

The composition according to the invention can comprise, in addition to the abovementioned anionic and nonanionic surfactants, at least one additional foaming agent chosen from amphoteric or zwitterionic surfactants, saponins and their mixtures, but only insofar as the presence of these surfactants does not affect the comfort (harmlessness) of the composition.

The amphoteric surfactants (this term including amphoteric and zwitterionic surfactants) can be chosen, for example, from betaines, N-alkyl amido betaines and their derivatives, glycine derivatives, sultaines, alkyl polyaminocarboxylates, alkylamphoacetates and their mixtures.

Mention may in particular be made, as betaines, of alkyl betaines, such as, for example, coco betaine, such as the product sold under the name Dehyton AB-30® by Cognis, lauryl betaine, such as the product sold under the name Genagen KB® by Clariant, oxyethylenated (10 EO) lauryl betaine, such as the product sold under the name Lauryl Ether (10 OE) Betaine® by Shin Nihon Rica, or oxyethylenated (10 EO) stearyl betaine such as product sold under the name Stearyl Ether (10 OE) Betaine® by Shin Nihon Rica.

Mention may be made, among N-alkyl amido betaines and their derivatives, for example, of cocamidopropyl betaine, sold under the name Lebon 2000 HG® by Sanyo, under the name Empigen BB® by Albright & Wilson or under the names Tego Betain F 50 and CK D by Evonik Goldschmidt, or those sold as a mixture with glyceryl laurate, such as the commercial references Tego Betain HS or Antil HS 60 from Evonik Goldschmidt, or lauramidopropyl betaine, sold under the name Rewoteric AMB12P® by Witco.

Mention may be made, as sultaines, of cocoylamidopropyl hydroxysulphobetaine, sold under the name Crosultaine C-500 by Croda.

Mention may be made, as alkyl polyaminocarboxylates (APACs) of sodium cocoylpolyaminocarboxylate, sold under the name Ampholak 7 CX/C® and Ampholak 7 CX® by Akzo Nobel, sodium stearylpolyamidocarboxylate, sold under the name Ampholak 7 TX/C by Akzo Nobel or sodium carboxymethyloleylpolypropylamine, sold under the name Ampholak XO7/C® by Akzo Nobel.

Mention may be made, as alkylamphoacetates, for example, of N-disodium N-cocoyl-N-carboxymethoxyethyl-N-(carboxymethyl)ethylenediamine (CTFA name: disodium cocamphodiacetate), such as the product sold under the name Miranol C2M Concentré NP® by Rhodia Chimie, and N-sodium N-cocoyl-N-hydroxyethyl-N-(carboxymethyl)ethylenediamine (CTFA name: sodium cocamphoacetate).

The saponins can preferably be chosen from the saponins extracted from soapnut trees (*Sapindus mukorossi, Sapindus trifoliatus, Sapindus saponaria*), liquorice (*Glycyrrhiza glabra*), horse chestnut (*Aesculus hippocastanum*), water hyssop (*Bacopa monnieri*), sarsaparilla (*Smilax medica, Smilax aspera, Smilax ornata*), Panama wood (*Quillaja saponaria*), common soapwort (*Saponaria officinalis*), ginseng (*Panax ginseng*), yucca (*Yucca schidigera*), puncture vine (*Tribulus terrestris*), juazeiro (*Ziziphus joazeiro*), jiaogulan (*Gynostemma pentaphyllum*), Indian asparagus (*Asparagus racemosus*), alfalfa (*Medicago sativa*) and their mixtures.

According to one embodiment, the composition comprises at least one additional foaming agent chosen from saponins.

The additional foaming agents can be present in a content ranging from 0.1 to 20% by weight, preferably from 0.5 to 15% by weight, better still from 1 to 10% by weight and even better still from 2 to 8% by weight, with respect to the total weight of the composition.

Particles

The particles are present in the composition according to the invention in a content of greater than or equal to 25% by weight, with respect to the total weight of the composition, preferably of greater than or equal to 30% by weight and better still of greater than or equal to 35% by weight.

The amount of particles can range from 25 to 90% by weight, better still from 30 to 80% by weight and even better still from 35 to 75% by weight, with respect to the total weight of the composition.

Fillers

"Fillers" should be understood as meaning solid particles which are insoluble in the medium of the composition, whatever the temperature at which the composition is manufactured.

The fillers can be colourless or white and inorganic or organic, of any physical shape (platelet, spherical or oblong) and of any crystallographic form (for example sheet, cubic, hexagonal, orthorhombic and the like). The fillers can be porous or nonporous.

Mention may be made, as fillers, of inorganic fillers, such as silica, clays, ceramic beads, calcium carbonate, titanium oxides, talc or magnesium silicate (particle size: 5 microns), sold under the name Luzenac 15 MOO® by Luzenac or talcs sold under the names Luzenac 00 and Luzenac Pharma M by Luzenac, kaolin or aluminium silicate, such as, for example, that sold under the name Kaolin Supreme® by Imerys, or sand with a particle size of between 1 and 1000 microns, or organic fillers, such as starches, such as, for example, the product sold under the name Mais Starch B® by Roquette, maize starch, Natpure Hollow Bead or Cellulobead D-10 spheres, Nylon microspheres, such as those sold under the name Orgasol 2002 UD NAT COS® by Atochem, microspheres based on vinylidene chloride/acrylonitrile/methacrylonitrile copolymer including isobutane, expanded microspheres, such as those sold under the name Expancel 551 DE® by Expancel, micronized or nonmicronized plant powders, such as the fruit powders from Lessonia or bamboo powders, or rice grain husk powder, and their mixtures.

Mention may also be made, as fillers, of exfoliating particles which will make possible scrubbing of the skin. Use may be made, as exfoliating particles, of exfoliating or scrubbing particles of mineral, vegetable or organic origin. Thus, use may be made, for example, of polyethylene beads or powder, such as those sold under the name Microthene MN 727 or Microthene MN 710-20 by Equistar or such as the powders sold under the name Gotalene 120 Colorless 2 by Dupont; Nylon particles, such as those sold by Arkema under the name Orgasol 2002 Exd Nat Cos; poly(vinyl chloride) powder; pumice (INCI name) such as pumice 3/B from Eyraud; ground fruit kernel shells, such as ground materials derived from apricot kernels or walnut shells; sawdust, wood flour or cork flour; glass beads; alumina (aluminium oxide) (INCI name: Alumina), such as the product sold under the name Dermagrain 900 by Marketech International; sugar crystals; beads which melt during application on the skin, such as, for example, spheres based on mannitol and cellulose which are sold under the Unisphere names by Induchem, agar-based capsules which are sold under the Primasponge names by Cognis and spheres based on jojoba esters which are sold under the Florasphéres names by Floratech; and their mixtures.

According to one embodiment, the composition according to the invention comprises at least one filler chosen from talc, kaolin, plant powders, such as rice grain husk powder, and their mixtures.

According to one embodiment, the fillers are present in the composition according to the invention in a content of greater than or equal to 25% by weight, with respect to the total weight of the composition, preferably of greater than or equal to 30% by weight and better still of greater than or equal to 35% by weight. The amount of fillers can range from 25 to 90% by weight, better still from 30 to 80% by weight and even better still from 35 to 75% by weight, with respect to the total weight of the composition.

Fibres

According to one embodiment, the composition according to the invention comprises fibres which can make it possible to improve the disintegration of the composition, the initiation of foam and the quality of the foam.

"Fibre" should be understood as meaning an object with a length L with a diameter D such that L is greater than D and preferably much greater than D, D being the diameter of the circle in which the cross section of the fibre appears. In particular, the ratio L/D (or aspect ratio) is chosen in the range extending from 3.5 to 2500, preferably from 5 to 500, and better still from 5 to 150.

The fibres which can be used in the composition of the invention can be fibres of synthetic or natural and inorganic or organic origin, and they can be flexible or stiff. They can be short or long, individual or organized, for example braided. They can have any shape and can in particular have a circular or polygonal (square, hexagonal or octagonal) cross section, according to the specific application envisaged. In particular, their ends are blunted and/or smoothed in order to avoid inflicting injury.

In particular, the fibres have a length ranging from 1 µm to 10 mm, preferably from 0.1 mm to 5 mm and better still from 0.1 mm to 3 mm. They have a cross section included within a circle with a diameter ranging from 2 nm to 500 µm, preferably ranging from 100 nm to 100 µm. The weight of the fibres is often given in denier or decitex.

The fibres can be those used in the manufacture of textiles and in particular fibres of silk, cotton, bamboo, wool or flax, cellulose fibres extracted, for example, from wood, vegetables or algae, fibres of polyamide (Nylon®), in particular under the names Nylon 6=Polyamide 6; Nylon 6,6 or Nylon 66=Polyamide 6,6; Nylon 12=Polyamide 12), rayon, viscose, acetate in particular rayon acetate, cellulose acetate or silk acetate, poly(p-phenylene terephthalamide) or acrylic polymer, in particular poly(methyl methacrylate) or poly(2-hydroxyethyl methacrylate), fibres of polyolefin and in particular of polyethylene or polypropylene, fibres of glass, silica, carbon, in particular in the graphite form, polytetrafluoroethylene (such as Teflon®), insoluble collagen, polyesters, poly(vinyl chloride), poly(vinylidene chloride), poly (vinyl alcohol), polyacrylonitrile, chitosan, polyurethane or poly(ethylene phthalate), fibres formed from a blend of polymers such as those mentioned above, for example polyamide/polyester fibres, and the blends of these fibres.

Use may also be made of surgical fibres, such as resorbable synthetic fibres prepared from glycolic acid and caprolactone ("Monocryl" from Johnson & Johnson); resorbable synthetic fibres of the copolymer of lactic acid and of glycolic acid type ("Vicryl" from Johnson & Johnson); poly(terephthalic ester) fibres ("Ethibond" from Johnson & Johnson) and stainless steel wires ("Steel Wire" from Johnson & Johnson).

Furthermore, the fibres may or may not be surface-treated and may or may not be coated. Mention may be made, as coated fibres which can be used in the invention, of polyamide fibres coated with copper sulphide for an antistatic effect (for example, the R-STAT fibres from Rhodia) or fibres coated with another polymer which makes possible a particular arrangement of the fibres (specific surface treatment) or a surface treatment which brings about effects of colours/holograms ("Lurex" fibre from Sildorex, for example).

The fibres which can be used in the composition according to the invention are preferably chosen from polyamide fibres, cellulose fibres, polyethylene fibres and their mixtures. Their length can range from 0.1 to 5 mm, preferably from 0.25 to 1.6 mm, and their mean diameter can range from 5 to 50 μm.

According to a preferred embodiment of the invention, the fibres are chosen from cellulose fibres.

Mention may be made of the polyamide fibres sold by Etablissements P. Bonte under the name Polyamide 0.9 Dtex 0.3 mm (INCI name: Nylon 6,6), having a mean diameter of 6 μm, a weight of approximately 0.9 dtex and a length ranging from 0.3 mm to 3 mm, or alternatively of the polyamides fibres sold under the name Fiberlon 931-D1-S by LCW, having a count of approximately 0.9 Dtex and a length of approximately 0.3 mm. Use may also be made of the Nylon-66 fibres, having a count of approximately 2 Dtex and a length of approximately 0.3 mm, sold under the name "Polyamide brillante trilobée" by Utexbel (INCI name: Nylon-66).

Use may also be made of cellulose fibres (or rayon fibres) having a mean diameter of 50 μm and a length ranging from 0.5 mm to 6 mm, such as those sold under the name "Natural rayon flock fiber RC1 BE-N003-M04" by Claremont Flock. Use may also be made of polyethylene fibres, such as those sold under the name "Shurt Stuff 13 099 F" by Mini Fibers.

The fibres can be present in a content ranging from 0.1 to 30% by weight, preferably from 0.5 to 25% by weight, better still from 1 to 15% by weight and even better still from 1 to 5% by weight, with respect to the total weight of the composition.

According to one embodiment, the composition according to the invention comprises particles and fibres.

Binding Agents

The composition according to the invention advantageously comprises at least one binding agent chosen from:
polyols, such as glycerol, 1,3-propanediol, propylene glycol, butylene glycol, hexylene glycol, polyethylene glycols, such as PEG-8 or dipropylene glycol,
sugars, such as mannitol, maltodextrin, the sorbitol, xylitol, sucrose or glucose, and their mixtures.

The binding agent can represent from 3 to 80% by weight, with respect to the total weight of the composition, preferably from 5 to 70% by weight, with respect to the total weight of the composition, and at best from 7 to 65% by weight.

The compositions of the invention can comprise adjuvants normally used in the cosmetics field and in particular those used in cleansing products. Mention may be made, as adjuvants, for example, of fragrances, preservatives, sequestering agents (EDTA, sodium phytate), effervescent agents such as sodium bicarbonate, pigments, pearlescent agents, soluble dyes, sunscreens, cosmetic or dermatological active principles, such as water-soluble or fat-soluble vitamins, antiseptics, antiseborrhoeics, antimicrobials, such as benzoyl peroxide, salicylic acid, triclosan, azelaic acid, and also optical brighteners, nonionic polymers, such as polyvinylpyrrolidone (PVP), anionic polymers or fatty substances, such as oils or waxes.

The amounts of these various adjuvants are those conventionally used in the field under consideration, for example from 0.01 to 20% of the total weight of the composition. These adjuvants and their concentrations must be such that they do not modify the property desired for the composition of the invention.

Mention may be made, as active principles, of any care or cleansing active principle normally used in the cosmetics field, in particular antibacterials, such as octopirox and triclosan, keratolytic agents, such as salicylic acid, lactic acid or glycolic acid, essential oils or vitamins, such as vitamin C (ascorbic acid), vitamin A (retinol), vitamin PP (niacinamide), vitamin B3 (panthenol) and their derivatives.

The compositions according to the invention can constitute in particular products for cleansing or removing makeup from the skin (body, face, eyes), scalp and/or hair.

Another subject-matter of the invention is a method for cleansing or removing makeup from keratinous substances, such as the skin, including the scalp, keratinous fibres, such as the eyelashes or hair, and/or lips, characterized in that a cosmetic composition as defined above is applied to the said keratinous substances.

Another subject-matter of the invention consists of the cosmetic use of the composition as defined above as product for cleansing and/or removing makeup from keratinous substances.

Another subject-matter of the invention consists of a cosmetic method for cleansing keratinous substances, characterized in that the composition of the invention is applied to keratinous substances in the presence of water and in that the foam formed and the grime are removed by rinsing with water.

The compositions according to the invention are preferably in the solid form, that is to say that they do not flow under their own weight. In particular, they can be provided in the pulverulent form or in the form of a modelling clay or also in the solid form.

The following examples are given by way of illustration of the invention and do not have a limiting nature. All the amounts are given as percentage by weight, with respect to the total weight of the composition. The names of the compounds are indicated, as the case may be, as chemical names or as INCI names.

EXAMPLES

Example 1

Foaming Composition in the Form of a "Modelling Clay"

| Phase A | Propylene glycol | 29.4 |
|---|---|---|
| | Glycerin | 5 |
| | Sucrose laurate (Surfhope SE Cosme C-1216 from Mitsubishi Kagaku Foods Corp.) | 7 |
| | Fragrance | 0.1 |
| Phase B | Sodium lauroyl glutamate (Amisoft LS 11 (Ajinomoto)) | 5 |
| | Kaolinite (Kaolin Polwhite B from Imerys) | 10 |
| | Cellulose fibres (Elcema F 150 from Rettenmaier, 150 microns) | 2.5 |
| | Rice grain husk powder (Ricesilk from Soliance) | 5 |
| | Titanium oxide | 1 |
| | Talc (4.5 microns) (Imperial 400 (3478 H) from Luzenac) | 35 |

Procedure

Phase A: The sucrose laurate is dissolved in the propylene glycol and the glycerin while stirring at slow speed with a deflocculating paddle.

Phase B: At the same time, the powders are mixed with the sodium lauroyl glutamate while stirring with a mixer for approximately two minutes.

Phase A is added to phase B while continuing to stir using a stirrer or mixer.

The above composition mixes well with water and exhibits good foaming properties.

Example 2

Foaming Composition in the Pulverulent Form

| Phase A | Propylene glycol | 9.4 |
|---|---|---|
| | Glycerin | 5 |
| | Sucrose laurate (Surfhope SE Cosme C-1216 from Mitsubishi Kagaku Foods Corp.) | 7 |
| | Fragrance | 0.1 |
| Phase B | Sodium lauroyl glutamate (Amisoft LS 11 from Ajinomoto) | 5 |
| | Kaolinite (Kaolin Polwhite B from Imerys) | 10 |
| | Cellulose fibres (Elcema F 150 from Rettenmaier, 150 microns) | 2.5 |
| | Rice grain husk powder (Ricesilk from Soliance) | 5 |
| | Titanium oxide | 1 |
| | Talc (4.5 microns) (Imperial 400 (3478 H) from Luzenac) | 55 |

Procedure

Phase A: The sucrose laurate is dissolved in the propylene glycol and the glycerin while stirring with a mixer-extruder or a Baker Perkins.

Phase B: At the same time, the powders are mixed with the sodium lauroyl glutamate while stirring with a mixer-extruder or a Baker Perkins for approximately 10-20 minutes.

Phase A is added to phase B while continuing to stir.

The invention claimed is:

1. A foaming, anhydrous cosmetic composition comprising, in a physiologically acceptable medium:
    at least one nonionic surfactant,
    at least one anionic surfactant,
    at least one binding agent selected from the group consisting of glycerol, 1,3-propanediol, propylene glycol, butylene glycol, hexylene glycol, polyethylene glycol(s), and mixtures thereof, and
    at least one particle selected from the group consisting of polyamide fibers, cellulose fibers, polyethylene fibers, and mixtures thereof, wherein the at least one particle is present in an amount of 0.1 to 30% by weight, with respect to a total weight of the composition, and
    optionally at least one additional particle selected from the group consisting of fillers, additional fibers, and mixtures thereof,
    wherein the combined total amount of fibers and fillers present in the composition is at least 25% by weight with respect to the total weight of the composition.

2. The composition of claim 1, wherein the nonionic surfactant is at least one selected from the group consisting of a phospholipid, an alkyl polyglucoside, a maltose ester, a sucrose ester, a hydrophobicized gum, a polyglycerolated fatty alcohol, an ester of glycerol and of a fatty acid, an oxyalkylenated glycerol ester, an oxyalkylenated sugar ester, a polyethylene glycol fatty acid ester, an ester of a fatty acid and of sorbitan, and a glucamine derivative.

3. The composition of claim 1, wherein the nonionic surfactant is an ester of sucrose and of a fatty acid.

4. The composition of claim 3, wherein the fatty acid comprises 10 to 24 carbon atoms.

5. The composition of claim 3, wherein the fatty acid is at least one selected from the group consisting of oleic acid, lauric acid, palmitic acid, myristic acid, stearic acid, linoleic acid, and capric acid.

6. The composition of claim 3, wherein the ester of sucrose and of a fatty acid is sucrose laurate, sucrose palmitate, or a mixture of both.

7. The composition of claim 1, wherein an amount of the nonionic surfactant is 0.1 to 20% by weight, with respect to a total weight of the composition.

8. The composition of claim 1, wherein the anionic surfactant is at least one selected from the group consisting of an anionic derivative of a protein of vegetable origin, an amino acid, an amino acid derivative, an alkyl sulfate, an alkyl ether sulfate, a sulfonate, an isethionate, a taurate, a sulfosuccinate, an alkyl sulfoacetate, a phosphate, an alkyl phosphate, a polypeptide, an anionic derivative of alkyl polyglucoside, a soap, a salt of a fatty acid, a soybean oil derivative, a lactic acid derivative, and a salt thereof.

9. The composition of claim 1, wherein the anionic surfactant is an alkali metal salt of a $(C_{10}\text{-}C_{22})$acylglutamic acid.

10. The composition of claim 1, wherein an amount of the anionic surfactant is 0.1 to 20% by weight, with respect to a total weight of the composition.

11. The composition of claim 1, wherein the combined total amount of fibers and fillers is greater than or equal to 30% by weight.

12. The composition of claim 1, wherein the combined total amount of fibers and fillers is 25 to 90% by weight, with respect to a total weight of the composition.

13. The composition of claim 1, further comprising fillers.

14. The composition of claim 1, further comprising at least one filler selected from the group consisting of talc and kaolin.

15. The composition of claim 1, comprising at least one fiber selected from the group consisting of a cellulose fiber and a polyethylene fiber.

16. The composition of claim 15, wherein the fiber is present in a content of 0.5 to 25% by weight, with respect to a total weight of the composition.

17. The composition of claim 1, wherein the binding agent represents from 3 to 80% by weight, with respect to the total weight of the composition.

18. A method for cleansing or removing makeup from a keratinous substance, the method comprising applying the cosmetic composition of claim 1 to the keratinous substance.

19. The composition of claim 1, wherein an amount of the nonionic surfactant is 2 to 8% by weight, with respect to a total weight of the composition.

20. The composition of claim 1, wherein the composition is in solid form.

21. The composition of claim 1, wherein the composition is in pulverulent form.

22. The composition of claim 1, wherein the composition is a modeling clay.

* * * * *